US00PP34718P3

(12) United States Plant Patent
Schulze et al.

(10) Patent No.: US PP34,718 P3
(45) Date of Patent: Nov. 8, 2022

(54) BLUEBERRY PLANT NAMED 'RB A063'

(50) Latin Name: ***Vaccinium corymbosum* L.**
Varietal Denomination: RB A063

(71) Applicant: Royal Berries S.L.U., Almonte (ES)

(72) Inventors: Philipp Schulze, Seville (ES); José Ulf Hayler López, Tomares (ES)

(73) Assignee: ROYAL BERRIES S.L.U., Almonte (ES)

( * ) Notice: Subject to any disclaimer, the term of this patent is extended or adjusted under 35 U.S.C. 154(b) by 0 days.

(21) Appl. No.: 17/585,906

(22) Filed: Jan. 27, 2022

(65) Prior Publication Data

US 2022/0248579 P1 Aug. 4, 2022

(30) Foreign Application Priority Data

Jan. 29, 2021 (QZ) ..... PBR 20210331

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Buchanan Ingersoll & Rooney P.C.

(57) ABSTRACT

A new and distinct variety of blueberry plant named 'RB A063' is provided. 'RB A063' is a commercial low chill tetraploid southern highbush blueberry (*Vaccinium*) variety intended for the fresh fruit market. Thus, 'RB A063' is best suited for production in low chill climates similar to Southern Spain.

8 Drawing Sheets

Figure 1:
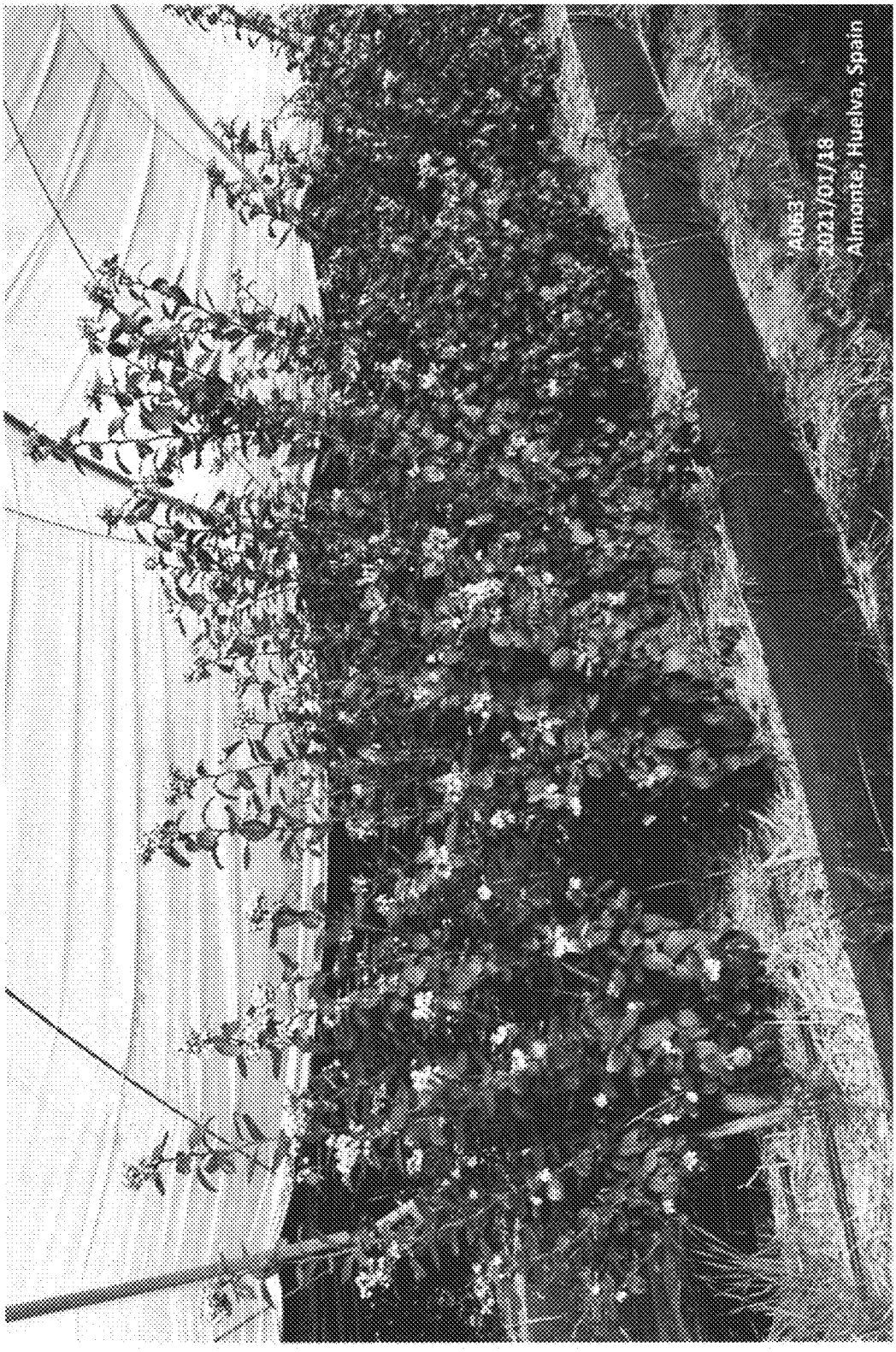

Botanical/commercial classification: Latin name: *Vaccinium corymbosum* L. Common name: Blueberry Plant.
Varietal denomination: 'RB A063'.

CROSS-REFERENCE TO RELATED APPLICATIONS

This application claims priority to Community Plant Variety Rights Application Number 2021/0331 which was filed in European Union through Community Plant Variety Office on Jan. 29, 2021, of which the content of is hereby expressly incorporated by reference in its entirety for all purposes.

SUMMARY OF THE INVENTION

The present invention relates to the discovery of a new and distinct variety of southern highbush blueberry, botanically known as *Vaccinium corymbosum* L. and herein referred to as 'RB A063'. The new blueberry variety of the present invention was the product of a controlled cross pollination carried out in Almonte, Huelva, Spain in 2006. The female parent (i.e. seed parent) was the proprietary variety 'Rocio' (U.S. Plant Pat. No. 20,374). The male parent (i.e. pollen parent) was the unreleased proprietary selection 'S124'. The parentage of the new variety can be summarized as follows:

'RB A063' was selected on the same location in 2012 for its early fruit ripening and outstanding fruit quality characteristics in terms of skin color, fruit size and organoleptic qualities. It was initially propagated by softwood cuttings from the original seedling in the same year and planted in first trials in 2014. Since then the new variety 'RB A063' has been reliably propagated asexually by softwood cuttings and was found to be stable.

'RB A063' is a tetraploid southern highbush blueberry (*Vaccinium*) variety with a chill requirement of below 300 hours. It is best suited for production in low chill climates similar to Southern Spain. 'RB A063' is intended for the fresh fruit market.

The following characteristics have been repeatedly observed in plants of the variety 'RB A063' growing in Almonte, Huelva, Spain and are determined to be the unique characteristics of the new blueberry plant variety 'RB A063':

(a) exhibits an early fruit ripening,
(b) a very light blue color with abundant surface wax (bloom);
(c) an excellent aromatic flavor.

The new variety can be readily distinguished from its ancestors. More specifically, when compared to its female parent, the proprietary variety 'Rocio' (U.S. Plant Pat. No. 20,374), 'RB A063' has a longer harvest period, lighter fruit color, lower firmness and a higher sugar-acid-ratio. When compared to its male parent, the proprietary selection 'S124', 'RB A063' has an earlier harvest start, larger fruit size, lighter fruit color, higher firmness, a better picking scar and better flavor. The new variety can also be readily distinguished from non-parental related similar varieties.

When compared to the southern highbush blueberry variety 'New Hanover' (U.S. Plant Pat. No. 19,990), 'RB A063' has a round-oblate fruit shape while 'New Hanover' fruit shape is oblate. When compared to the southern highbush blueberry variety 'Suziblue' (U.S. Plant Pat. No. 21,167), 'RB A063' has a very light blue fruit skin color while 'Suziblue' skin color is dark blue. When compared to the highbush blueberry variety 'Legacy' (not patented), 'RB A063' has an early fruit ripening while 'Legacy' produces fruit in late season.

BRIEF DESCRIPTION OF THE PHOTOGRAPHS

The accompanying photographs show typical specimens in full color of the foliage, flowering and fruit of the new variety of 'RB A063' in Almonte, Huelva, Spain. The colors are as nearly true as is reasonably possible in a color representation of this type. The color values cited in the detailed botanical description accurately describe the colors of the new blueberry variety.

FIG. 1—a photograph showing 3 year old plants of 'RB A063' during flowering and fruit formation. It displays the overall bush shape and vigor.

Figure 2:
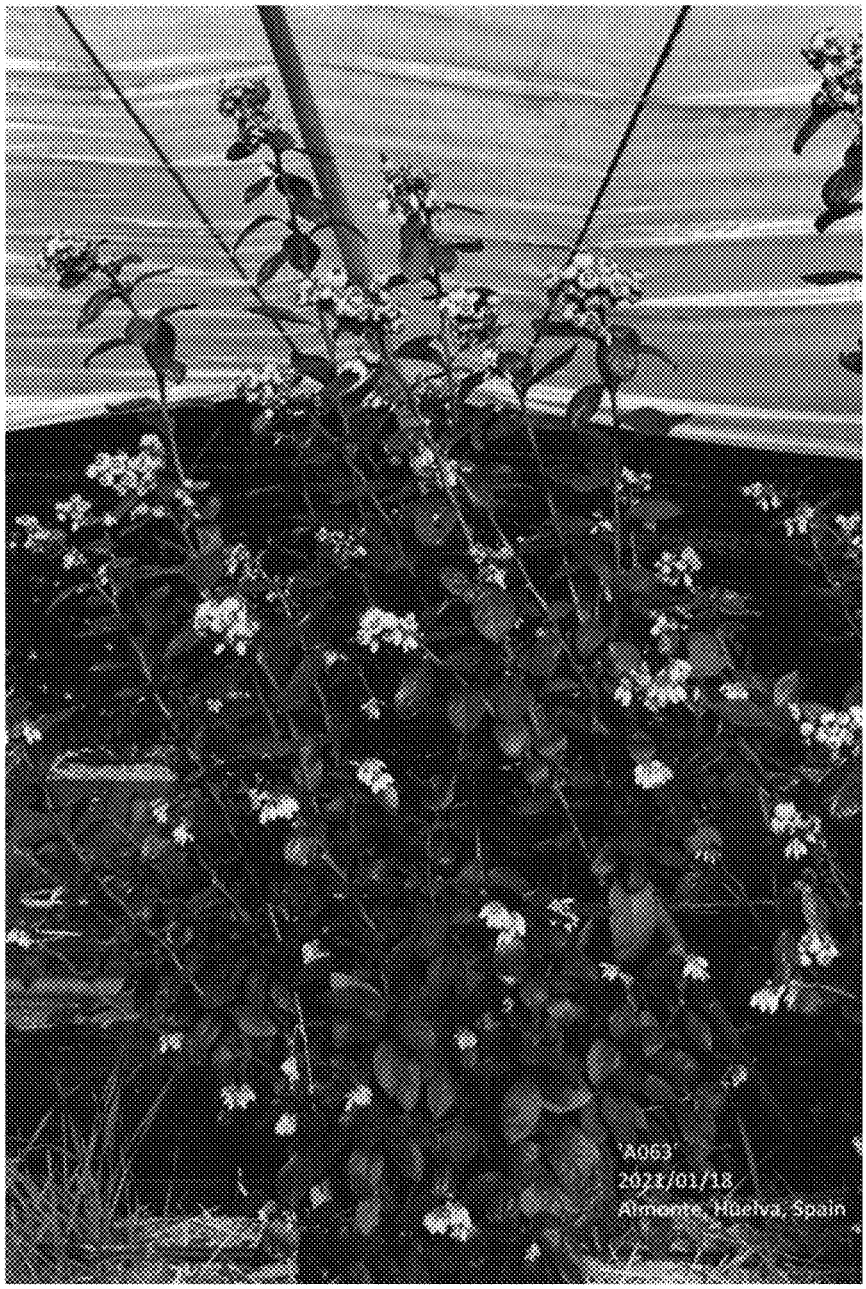

FIG. 2—a photograph showing a 3 year old plant of 'RB A063' during flowering and fruit formation. It displays the overall bush shape, leaf size and, color and structure of mature canes.

Figure 3:
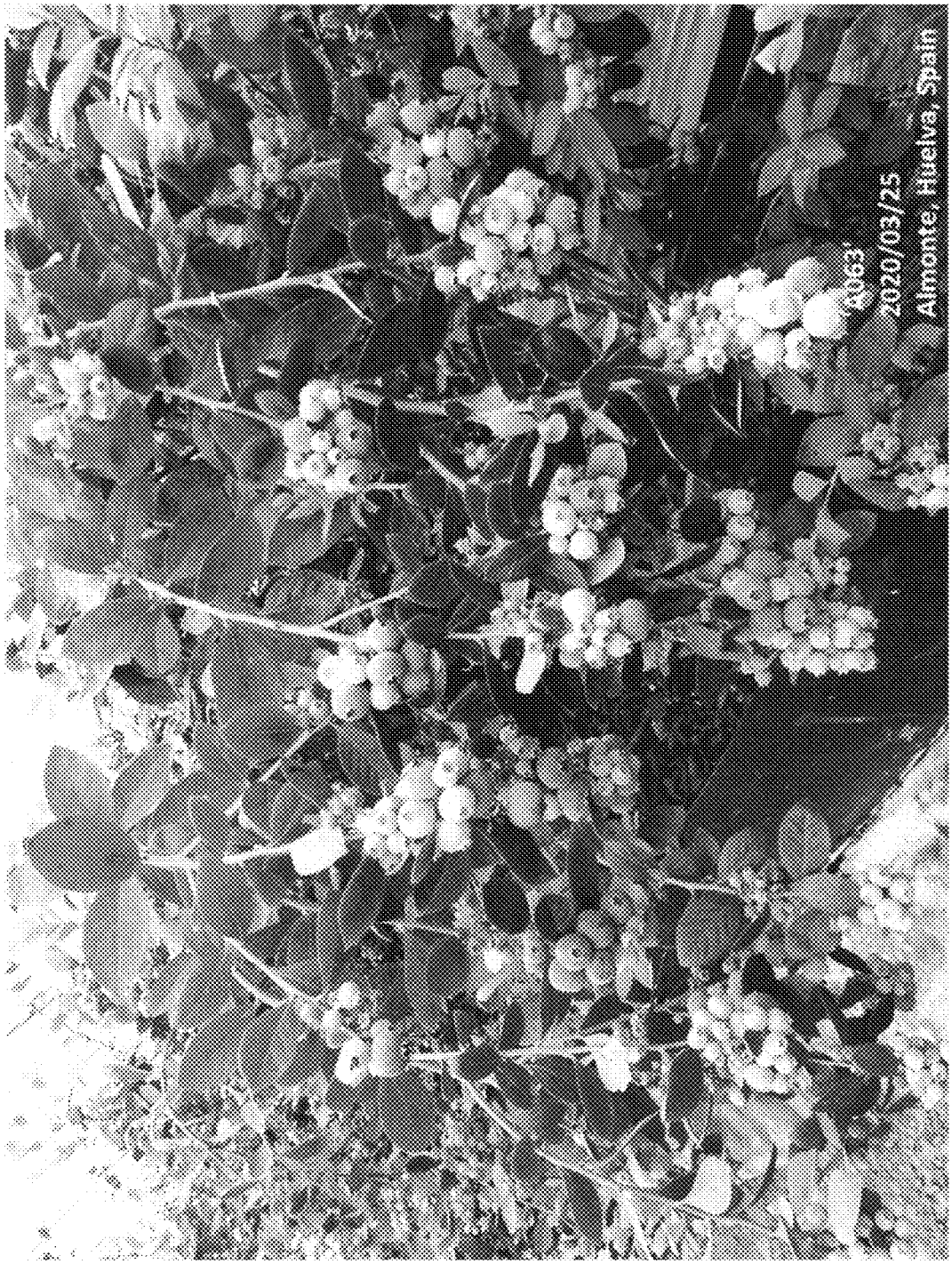

FIG. 3—a photograph of fruit clusters of 'RB A063' during fruit ripening, showing the presentation of the fruit and cluster density.

Figure 4:
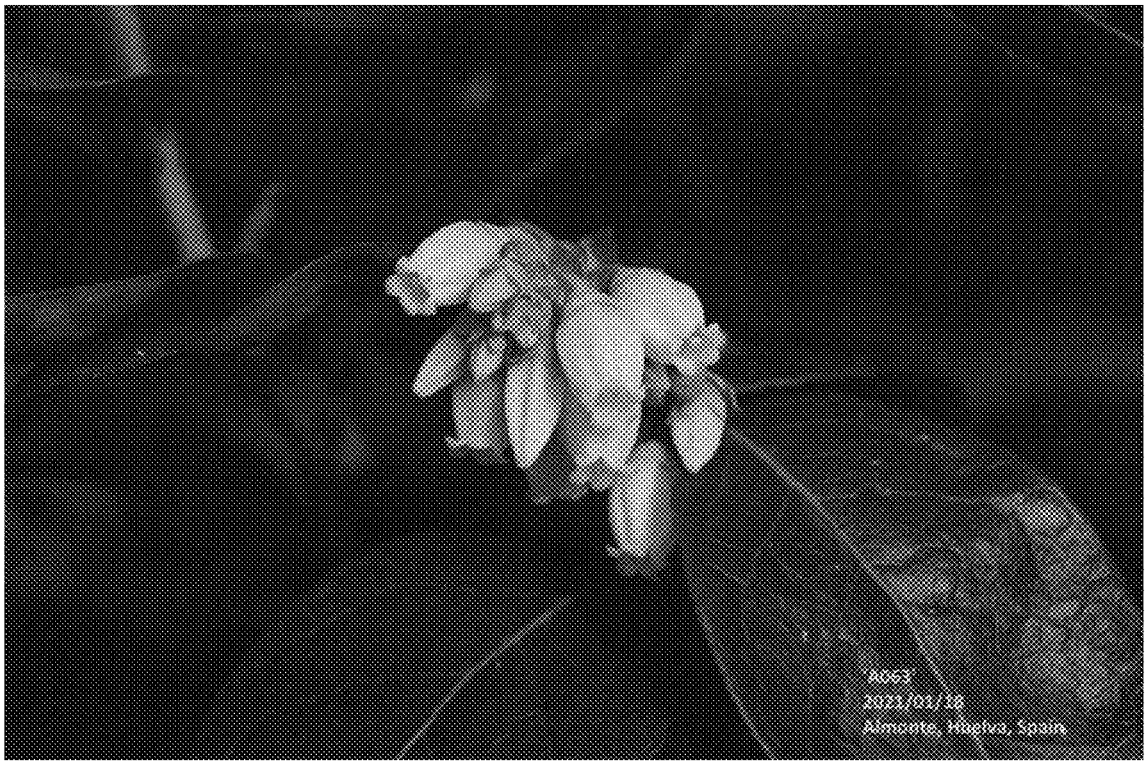

FIG. 4—a close-up photograph of a flower cluster of 'RB A063', shape and color of flowers and floral buds in different stages.

Figure 5:
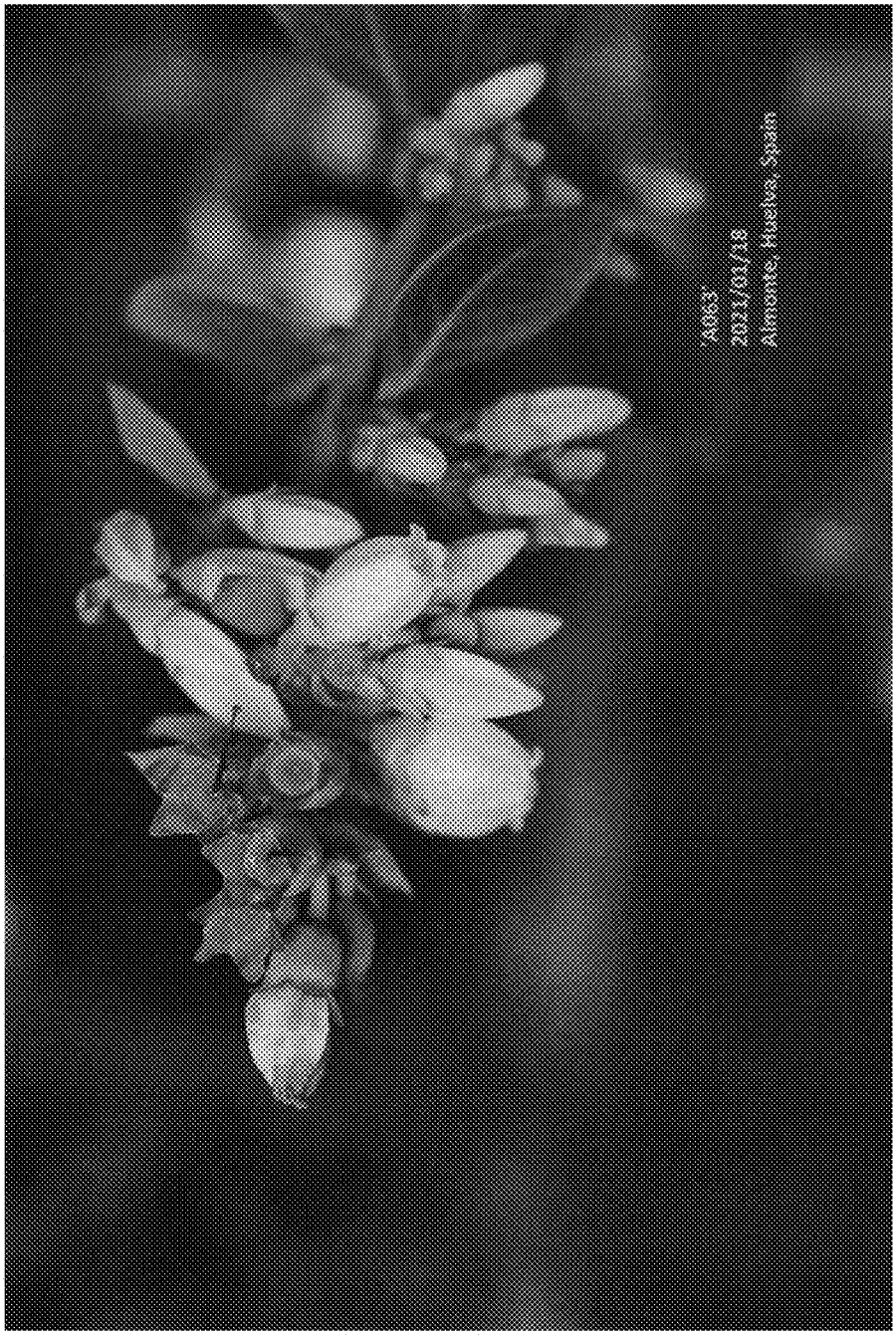

FIG. 5—a close-up photograph of a flower and fruit cluster of 'RB A063', showing the size, shape and color of flowers and immature fruit in different stages.

Figure 6:
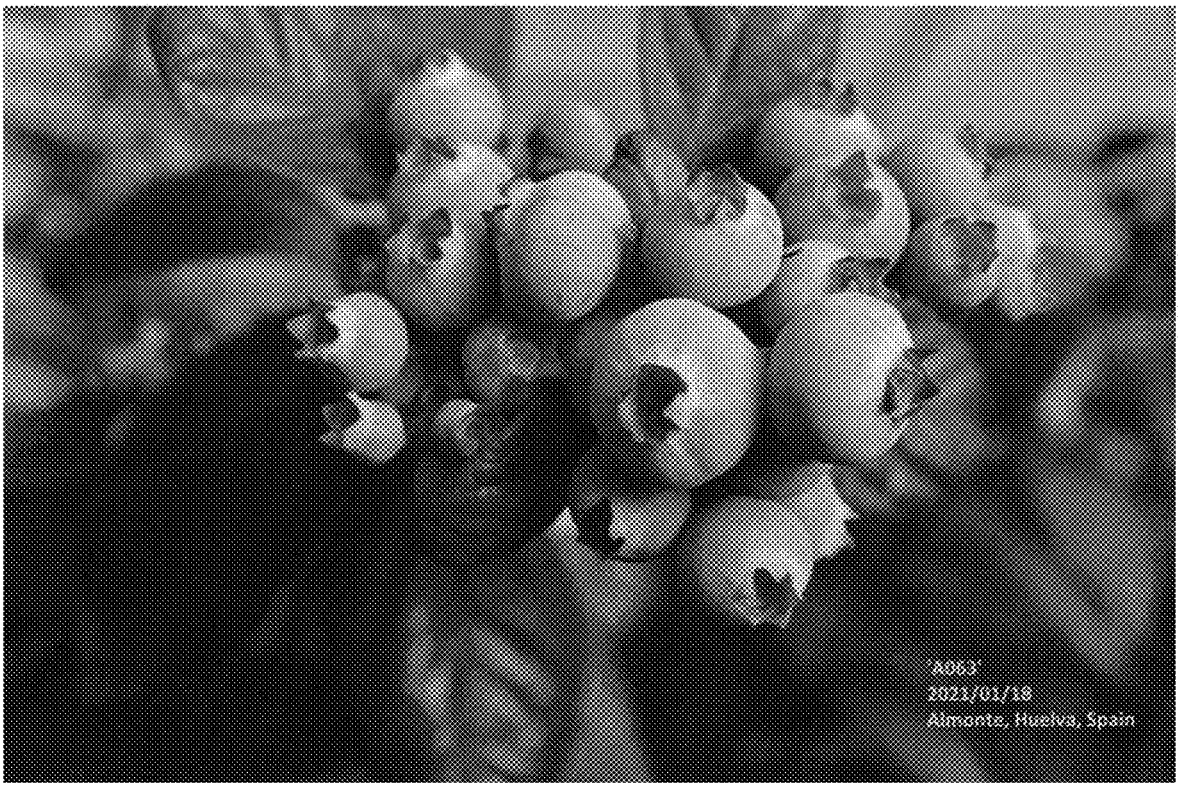

FIG. 6—a close-up photograph of a fruit cluster of 'RB A063', showing the size, shape and color of immature fruit in different stages.

Figure 7:
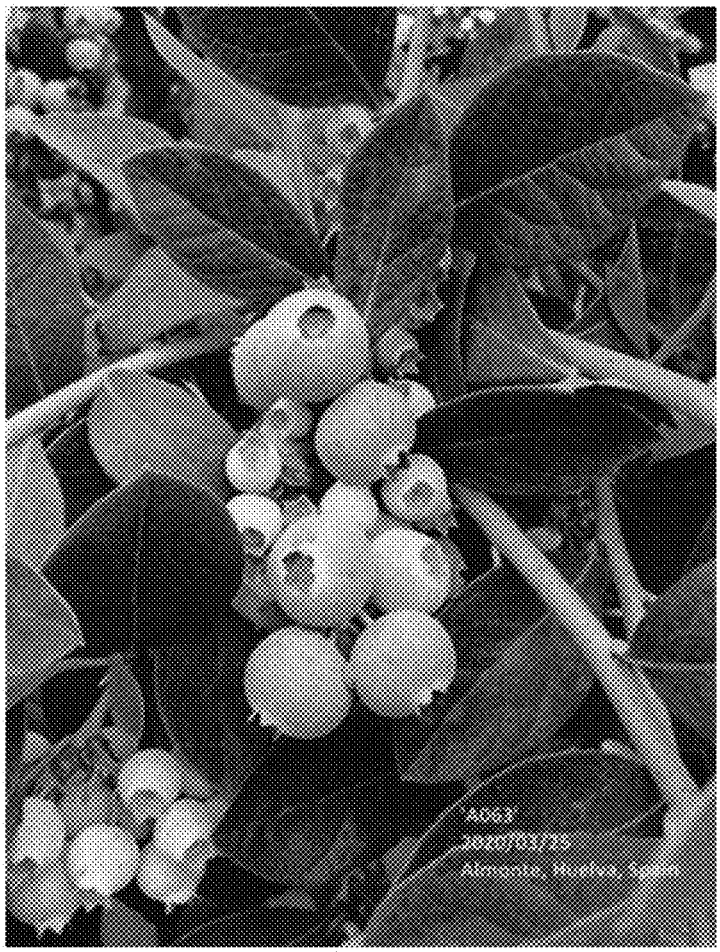

FIG. 7—a close-up photograph of a fruit cluster of 'RB A063', showing the size, shape and color of ripe and unripe fruit.

Figure 8:
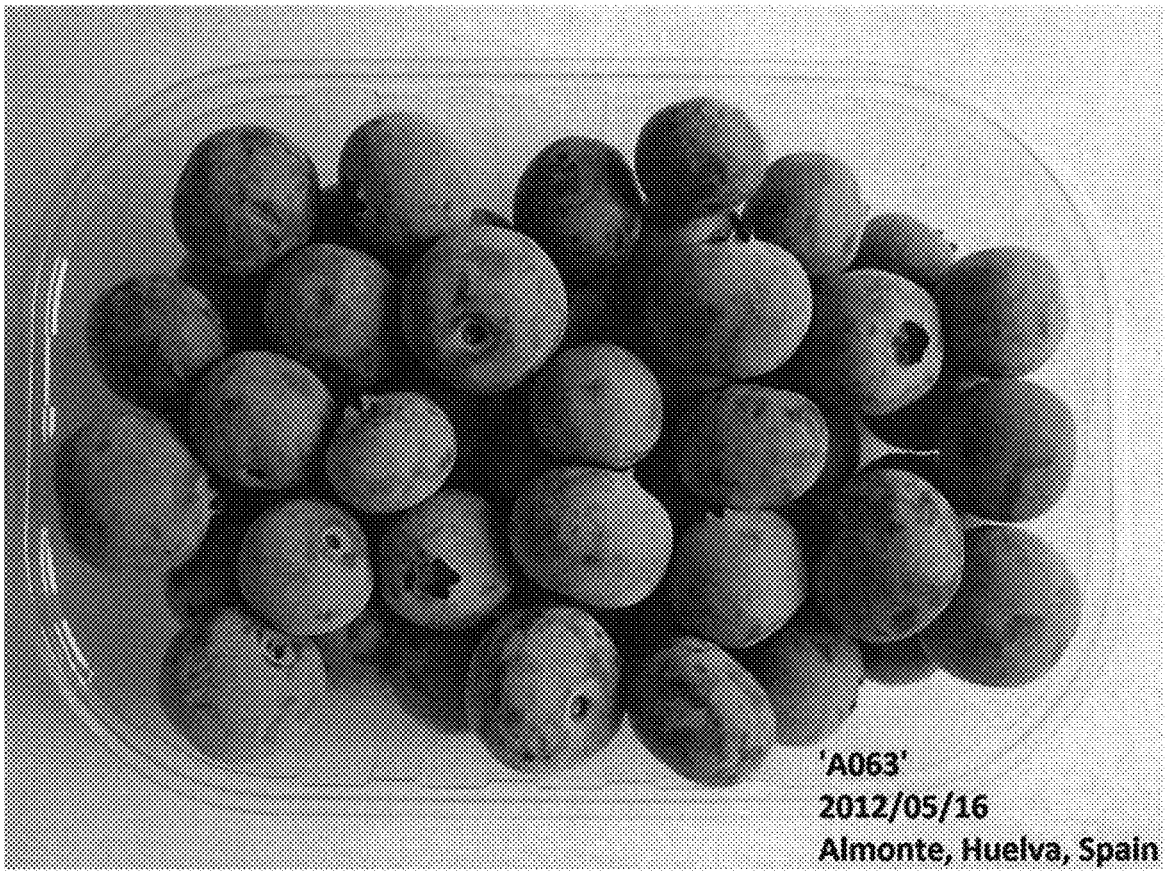

FIG. 8—a close-up photograph of harvest fruit of 'RB A063'.

DETAILED BOTANICAL DESCRIPTION

The botanical description reported herein were taken in Almonte, Huelva, Spain on 2 to 3-year-old plants during the years 2020 and 2021. The observations and measurements are average values calculated from a larger sample size. Where color codes are included, these are based upon The Royal Horticultural Colour Chart, 5$^{th}$ edition published in 2007 by The Royal Horticultural Society, London, England. Firmness was measured with a BioWorks FirmTech 2 Fruit Firmness Tester.

Plant:

*Growth habit.*—Semi-upright.
*Vigor.*—Strong.
*Plant width.*—Between 85-110 cm.
*Plant height.*—Between 120-160 cm.
*Branching.*—Moderate-high.
*Productivity.*—High: Average of 3.8 kg per plant on 2 years plants (Almonte, Spain).
*Cold hardiness/tolerance.*—Plant, flowers and fruit are hardy to −2° C. (Up to date, 'RB A063' has not been tested under cooler climate conditions.).
*Chilling requirement.*—<300 hours below 7° C.
*Tendency toward evergreenness.*—High.
*Ease of propagation.*—'RB A063' has been reliably propagated asexually by softwood cuttings and was found to be stable.
*Fruiting type.*—On one-year-old and current season's shoots.
*Resistance to disease.*—During the time of observations and to date, no exceptional sensitivities to any pest and disease were observed.

Trunk and branches:

*Immature cane length.*—About 47 cm.
*Immature cane diameter.*—About 20.3 mm.
*Immature cane color.*—Yellow-Green Group 144B.
*Immature cane texture.*—Smooth.
*Immature cane internode length.*—About 2 to 4 cm.
*Mature cane color.*—Grey-Brown Group N199C.
*Mature cane length.*—About 64 cm.
*Mature cane diameter.*—About 32.5 mm.
*Mature cane surface texture.*—Coarse.

Foliage:

*Time of beginning of bud burst.*—Approximately first week of February.
*Leaf length* (*without petiole*).—About 70 mm.
*Leaf width* (*at widest point*).—About 42 mm.
*Leaf length:width ratio.*—About 1.7.
*Leaf color* (*topside*).—Green Group 137A.
*Leaf color* (*underside*).—Green Group N138C.
*Leaf shape.*—Elliptic.
*Leaf margin.*—Entire.
*Leaf glaucosity on upper side.*—Present.
*Leaf pubescence on upper side.*—Absent.
*Leaf pubescence on lower side.*—Present.
*Leaf venation.*—Acute, moderately reticulated.
*Leaf apices.*—Generally acute, approximately 50°.
*Leaf bases.*—Acute, approximately 45°.
*Petiole length.*—About 3 mm to 5 mm.
*Petiole color.*—Yellow-Green Group 148C.
*Petiole pubescence.*—Present.

Flowers:

*Time of beginning of flowering on* 1-*year-old shoot.*—Approximately 3$^{rd}$ week of November.
*Flowering period.*—Approximately 17 weeks.
*Number of flower clusters per fruiting shoot.*—About 2 to 8, average: 6.8.
*Number of flowers per cluster.*—About 5 to 7.
*Fragrance.*—Absent.
*Shape.*—Urecolate.
*Immature flower color.*—Green-White Group157B.
*Immature flower anthocyanin coloration.*—Present, weak.
*Corolla color.*—White Group 155C.
*Corolla anthocyanin coloration.*—Present, weak.
*Corolla tube length.*—About 9.7 mm.
*Corolla tube width.*—About 4.2 mm.
*Corolla length:width ratio.*—About 2.3.
*Corolla aperture width.*—About 3.7 mm.
*Corolla ridges.*—Present.
*Number of petals.*—About 5.
*Petal length.*—About 11.2 mm.
*Petal width.*—About 2.6 mm.
*Peduncle color.*—Green Group 143C.
*Pedicle length.*—About 49 mm.
*Pedicle width.*—About 0.9 mm.
*Calyx diameter with sepals.*—About 3.9 mm.
*Calyx color.*—Yellow-Green Group 144B.
*Style length.*—About 9.9 mm.
*Style shape.*—Bottle shaped.

*Pistils.*—Some filaments adnates, hairs on filaments, only in the top middle; ratio pollensac:pollentube approximately 1:2.
*Pistil length.*—About 11.7 mm.
*Pistil color.*—Yellow-Green Group 144D.
*Ovary color.*—Yellow-Green Group 144D.
*Stamen length.*—About 6-7 mm.
*Number of stamen per flower.*—About 10.
*Filament color.*—Greyed-Orange Group N167A.
*Anther length.*—About 4 mm.
*Anther number.*—About 10.
*Anther color.*—Greyed-Orange Group 167A.
*Pollen abundance.*—Abundant.
*Pollen color.*—Yellow Group 8D.
*Self-compatibility.*—Moderate-high.
*Time of beginning of flowering on current season shoot.*—Approximately $2^{nd}$ week of June.

Fruit:

*General.*—Fruit observations were taken at peak production during 2020 and 2021.
*Time of beginning of fruiting on 1-year-old shoot.*—Approximately $2^{nd}$ week of February.
*Time of end of fruiting on 1-year-old shoot.*—Approximately beginning of June.
*Time of 50% fruiting on 1-year-old shoot.*—Approximately $15^{th}$ of May.
*Fruiting period on 1-year-old shoot.*—Approximately 15 weeks.
*Time of beginning of fruiting on current season shoot.*—Approximately beginning of July.
*Intensity of fruiting on current season shoots.*—Low.
*Fruiting cluster density.*—Dense.
*Surface color of unripe berry with wax (bloom).*—Yellow-Green Group 150C.
*Surface color of unripe berry without wax (bloom).*—Yellow-Green Group 150B.
*Surface color of mature berry with wax (bloom).*—Black Group 202B.
*Surface color of mature berry without wax (bloom).*—Black Group 203D.
*Surface wax (bloom) intensity.*—Very High.
*Berry flesh color.*—Green-Yellow Group 1C.
*Berry weight.*—About 3.08 g.
*Berry shape.*—Round-oblate.
*Picking scar.*—Small and dry.
*Berry calyx depth.*—Shallow.
*Berry calyx width.*—Narrow.
*Berry attitude of sepals.*—Incurving.
*Berry height.*—About 12.3 mm.
*Berry width.*—About 18.8 mm.
*Berry height:width ratio.*—About 0.7.
*Berry firmness.*—High (about 207.96 g/mm).
*Berry crunchiness.*—Low.
*Berry sweetness.*—High (12.96° Brix).
*Berry acidity.*—Medium (0.46% titratable acidity).
*Berry sweetness:acidity ratio.*—About 31.2 (ratio B/A).
*Berry texture.*—Fleshy and juicy.
*Berry flavor.*—Very good, aromatic.
*Storage quality.*—Very good.

Seed:

*Number per berry.*—About 43.
*Color.*—Greyed-Orange Group 164B.
*Dry weight (1000 seed).*—About 0.65 g.
*Shape.*—Elliptic.
*Length.*—About 1.1 to 2.0 mm.
*Width.*—About 0.4 to 0.5 mm.

Plants of the 'RB A063' variety have not been observed under all possible environmental conditions to date. Accordingly, it is possible that the phenotypic expression may vary somewhat under different climatic conditions and cultural practices.

We claim:

1. A new and distinct variety of southern highbush blueberry (*Vaccinium*) named 'RB A063', as illustrated and described herein.

* * * * *